United States Patent [19]

Watanabe et al.

[11] Patent Number: 5,347,056

[45] Date of Patent: Sep. 13, 1994

[54] PROCESS FOR PRODUCING UNSATURATED ALCOHOLS

[75] Inventors: Yoshihisa Watanabe; Mitsuhiko Kurashige, both of Inashiki, Japan

[73] Assignee: Mitsubishi Petrochemical Company, Ltd., Tokyo, Japan

[21] Appl. No.: 101,746

[22] Filed: Aug. 4, 1993

[30] Foreign Application Priority Data

Aug. 7, 1992 [JP] Japan .................................. 4-211573

[51] Int. Cl.$^5$ ...................... C07C 27/00; C07C 29/14; C07C 33/03; C07C 33/20
[52] U.S. Cl. .................................... 568/881; 568/813
[58] Field of Search ................................ 568/881, 813

[56] References Cited

U.S. PATENT DOCUMENTS

| | | | |
|---|---|---|---|
| 1,158,217 | 10/1915 | Hibbert | 568/881 |
| 1,895,515 | 1/1933 | Lazier | 568/881 |
| 2,767,221 | 10/1956 | Ballard et al. | 568/881 |
| 4,731,488 | 3/1988 | Shimasaki et al. | 568/881 |

*Primary Examiner*—Joseph E. Evans
*Attorney, Agent, or Firm*—Oblon, Spivak, McClelland, Maier & Neustadt

[57] ABSTRACT

This invention relates to a process for producing α,β-unsaturated alcohol, which uses unsaturated aldehyde as a starting material, and in which only the aldehyde group in the unsaturated aldehyde is selectively hydrogenated by hydrogen transfer reaction, while the carbon-carbon double bond is left as it is. The method is characterized by using a catalyst which contains at least one oxide selected from the group consisting of oxides of yttrium, lanthanum, praseodymium, neodymium and samarium, as a main active ingredient. The catalysts exhibit high activity and selectivity, as well as a long life span.

21 Claims, No Drawings

PROCESS FOR PRODUCING UNSATURATED ALCOHOLS

BACKGROUND OF THE INVENTION

1. Field of the Invention

The present invention relates to a process for producing an unsaturated alcohol, in which an unsaturated aldehyde is hydrogenated to give a corresponding unsaturated alcohol in the presence of a novel catalyst. In particular, the present invention relates to a process for producing an $\alpha, \beta$-unsaturated alcohol, in which an unsaturated aidehyde is used as a starting material, and only the aidehyde group in the unsaturated aidehyde is selectively hydrogenated by hydrogen transfer reaction from an alcohol in the presence of a catalyst containing the specific metallic oxide as an active ingredient, while leaving the carbon-carbon double bond as it is, to give the corresponding $\alpha, \beta$-unsaturated alcohol.

2. Description of the Prior Art

An unsaturated aidehyde has both a carbon-carbon double bond and a carbonyl group as functional groups in the same molecule. However, it is extremely difficult to selectively reduce only one of the functional groups. In particular, in the case of an $\alpha, \beta$-unsaturated carbonyl compound in which a double bond and a carbonyl group have a conjugated relationship with each other, an alkenyl group hydrogenates more easier than the carbonyl group. Therefore, in such case, the by-products of hydrogenation, such as saturated aldehydes and saturated alcohols, or other various by-products of condensation reaction are produced, resulting in the greater difficulty in selective hydrogenation.

Various methods have been attempted to selectively hydrogenate the aldehyde group in $\alpha, \beta$-unsaturated aldehydes, such as acrolein, while leaving the unsaturated bond as it is, and to produce the corresponding $\alpha, \beta$-unsaturated alcohol in high yields.

Numerous direct hydrogenating methods have been proposed. For example, there is the long-standing method using noble metals of the platinum group as catalysts (W. F. Tuley, R. Adams, J. Am. Chem. Soc., 47, 3061 (1925)); methods using catalysts mainly composed of copper-cadmium (U.S. Pat. No. 2,763,696), silver-zinc (Japanese Patent Laid-open No. 47-13010) or silver-cadmium (Japanese Patent Laid-open No. 53-18506) as catalysts able to give relatively high yield; and improved methods thereof (Japanese Patent Laid-open Nos. 64-159054 and 64-1207041).

However, the catalysts used in these methods do not exhibit enough high selectivity for the hydrogenating reaction. In addition, many of such catalysts contain harmful compounds. Therefore, from a safety point of view, they have not been used in large amounts industrially.

On the other hand, methods taking the place of those above have also been attempted, in which unsaturated alcohols are synthesized by utilizing the hydrogen transfer reaction from alcohol as a hydrogen source.

For example, there have been proposed methods using catalysts, such as catalysts containing alkali metals and alkaline earth metals, e.g., magnesium oxide, calcium oxide and lithium oxide, as active ingredients (S. A. Ballard et. al, "Advances in Catalysis" Vol. IX, Academic Press, (1957)); and catalysts represented by the general formula:

$$Mg_a X_b Y_c O_d$$

(in which X represents boron, aluminum, silicon, yttrium, niobium, lanthanum, etc., Y represents an alkali metal and/or an alkaline earth metal other than magnesium, O represents oxygen, and a, b, c and d are atomic ratios of Mg, X, Y and O, respectively) (Japanese Patent Laid-open No. 62-30552).

In addition, other silver-based catalysts used in direct hydrogenation have also been proposed (Japanese Patent Publication No. 51-42042).

However, the catalysts used in above methods exhibit low activity and selectivity, and the activity changes with the passage of time. Therefore, it is difficult to say that such catalysts have reached to an industrial level of use.

SUMMARY OF THE INVENTION

In order to solve the above problems, the present inventors have carried out a wide range of research concerning catalysts used for the production of unsaturated alcohols, in which an unsaturated aldehyde and an alcohol are supplied simultaneously to the catalyst layer, where hydrogen atom of the alcohol is donated to the unsaturated aldehyde to prepare an unsaturated alcohol.

As a result, the present inventors have surprisingly found that the catalysts containing at least one oxide selected from the group consisting of oxides of yttrium, lanthanum, praseodymium, neodymium and samarium as the main active ingredient, not only exhibit high activity and selectivity but also have a long life span against the reaction for the selective production of unsaturated alcohols. This result has led to the present invention.

That is, the present invention relates to a process for producing an unsaturated alcohol from an unsaturated aldehyde by using a hydrogen transfer reaction from an alcohol, which is characterized by using a catalyst that contains at least one oxide selected from the group consisting of oxides of yttrium, lanthanum, praseodymium, neodymium and samarium, as a main active ingredient, and further contains at least one oxide selected from the group consisting of oxides of manganese, calcium, strontium, chromium, magnesium, iron, cobalt, nickel, copper, zinc, zirconium, silver, cadmium, barium, cerium, lead, bismuth, boron, vanadium and tin.

DETAILED DESCRIPTION OF THE INVENTION

The main active ingredient and the supplementary active ingredient constituting the catalyst of the present invention are at least one element selected from the group consisting of yttrium, lanthanum, praseodymium, neodymium and samarium.

The catalyst of the present invention can contain at least one element selected from the group consisting of manganese, calcium, strontium, chromium, magnesium, iron, cobalt, nickel, copper, zinc, zirconium, silver, cadmium, barium, cerium, lead, bismuth, boron, vanadium and tin, as a supplementary ingredient.

In particular, catalysts containing yttrium as a main active ingredient and cobalt, zinc and/or manganese as a supplementary ingredient can give a preferable effect on the selectivity of the reaction and contribute to the improvement in yield of the objective products.

The form of such ingredients is preferably a soluble compound which can be converted into an oxide by hydrolysis or the following calcining process. Examples of such a compound include salts of inorganic or organic acids such as nitrates, sulfates, acetates, various kinds of halides, etc., and metallic organic compounds such as complex salts, chelate compounds, alkoxides, etc.

Preparation of Catalyst

The method for preparing the catalyst is not particularly limited, and any conventional method can be applied, so long as the method satisfies the requirement that the above active ingredients finally take the form of an oxide in which the ingredients are fully dispersed, such as impregnation methods, precipitation methods, coprecipitation methods, etc.

Also, any methods or steps for including the active ingredients in the catalysts can be applied arbitrarily, so long as the objects and the effects of the present invention are not substantially impaired.

For example, impregnation methods can be applied in which a precursor of a soluble active ingredient is impregnated in a pre-molded conventional porous carrier particles or fine powder, such as aluminum oxide, titanium oxide and zirconium oxide, followed by drying and calcining, to give a catalyst; and precipitation methods in which an active ingredient is precipitated from the aqueous solution of a salt of an active ingredient. In the latter method, the resulting catalyst precipitation can be used as it is, or by molding or calcining, or can be used by further supporting it on an appropriate carrier such as silica, alumina, etc.

At least one of the elements selected from the group consisting of yttrium, lanthanum, praseodymium, neodymium and samarium, constitutes the main ingredient of the catalyst of the present invention. The amount of such element to be used is within the range of 3 to 99.9 wt %, preferably 10 to 99.5 wt % of the total catalyst.

The active ingredient compound to be used is not necessarily in a pure form, and may be a so-called mixed rare earth elements which is a mixture of various kinds of rare earth elements so-called the mixed rare earth elements, and contains yttrium, etc. as a main component.

The supplementary active ingredients can be added in an arbitrary amount, so far as the amount is less than 50% of the main active ingredients.

The form of "catalyst" according to the present invention may be powdery or molded. Examples of the molded form are pillar-like, tablet, particulate, granular and plate forms.

The catalysts thus obtained have excellent properties in that high activity and high selectivity are maintained in the selective hydrogenating reaction of unsaturated aldehyde into unsaturated alcohols, even in long-duration continuous reactions.

Unsaturated aldehydes

In the present invention, as mentioned above, an unsaturated aldehyde is selectively hydrogenated to produce the corresponding unsaturated alcohol.

As the unsaturated aldehyde to be used in the present invention, there can be employed acrolein, methacrolein, crotonaldehyde, methyl vinyl ketone, cinnamaldehyde, and so on. In particular, the use of acrolein gives the most remarkable effect of the present invention.

Alcohols

The alcohol to be used as a hydrogen source in the present invention can be arbitrarily selected from primary and secondary alcohols, such as methanol, ethanol, isopropanol, 1-propanol, 1-butanol, 2-butanol, benzyl alcohol, isobutyl alcohol and cyclohexanol, by considering the availability, cost, the added value of the by-produced aldehyde and ketone, and so on.

Hydrogenating Reaction

The reaction in the method of the present invention can be carried out either in liquid phase or in vapor phase. In such reaction, the contact method can be appropriately selected from conventional known methods. For example, in the liquid phase reaction, a continuous or batchwise suspended bed method using a powdery catalyst can be employed. In the vapor phase method, not only the conventional fixed bed method, but also a fluidized bed method and a moving bed method can be employed.

In order to impart the characteristics of the present invention more effectively, the following reaction conditions are recommended:

The reaction temperature to be employed may be somewhat varied depending on the kinds of starting unsaturated aldehydes and alcohols, and so on, but is within the range of 100° to 500° C., preferably 200° to 400° C. When the temperature is lower than 100° C., the reaction rate of the unsaturated aldehyde is too low, which is not practical. On the other hand, when the temperature is greater than 500° C., the side reactions such as decomposition increase, resulting in a lowering of the selectivity of unsaturated alcohol, which is not desirable.

It is preferable that the molar ratio of alcohol/aldehyde be within the range of 0.1 to 20 and the flow rate (L.H.S.V) within the range of 0.01 to 1 $hr^{-1}$ (based on aldehyde).

In the reaction, the starting materials consisting of unsaturated aldehydes and alcohols can be supplied to the catalyst layer as is, or as mixed gases in which said starting materials are diluted with adequate diluents, such as nitrogen, steam, hydrogen, etc., if necessary.

Although the reaction pressure is not particularly critical, it is preferably within the range of atmospheric pressure to 50 $kg/cm^2$ in the gas phase reaction, and 10 to 100 $kg/cm^2$ in the liquid phase reaction.

As mentioned above, according to the present invention, there can be provided an epochmaking method for producing unsaturated alcohols using novel catalysts that do not contain the harmful substances such as cadmium, contained in conventional known catalysts and which show an extremely small lowering of activity with the passage of time and have high activity and selectivity in the reaction for producing unsaturated alcohols by hydrogenated reaction of unsaturated aldehydes.

EXAMPLES

The present invention will be illustrated in more detail by the following examples.

EXAMPLE 1

Preparation of Catalysts

An aqueous solution prepared by dissolving $Y(NO_3)_3 \cdot 6H_2O$ in 250 ml of pure water at 40° C., was added to 500 ml of an aqueous solution containing ammonium carbonate as a precipitant at 40° C. The resulting precipitate was filtered off, washed with pure water sufficiently, and then dried, followed by calcining at 600° C. for 2 hours.

To the resulting calcined powder, an adequate amount of pure water was added, to give a slurry. Then, the slurry was heat-kneaded to give a clayey material, and the resultant was subjected to extrusion molding, to give tablets with dimensions of $3\phi \times 5$ mm. After drying, the tablets were further calcined at 600° C. for 3 hours. The resultant was named Catalyst 1.

Other catalysts were prepared in the same manner as above, except that $La(NO_3)_3 \cdot 6H_2O$, $Pr(NO_3)_3 \cdot 6H_2O$, $Nd(NO_3)_3 \cdot 6H_2O$, $Sm(NO_3)_3 \cdot 6H_2O$, $Mg(NO_3)_3 \cdot 6H_2O$ and $Ce(NO_3)_3 \cdot 6H_2O$ were used instead of $Y(NO_3)_3 \cdot 6H_2O$ as a starting material. The resulting catalysts were named Catalysts 2 to 5, Comparative Catalyst 1 (MgO) and Comparative catalyst 2 ($Ce_2O_3$), respectively.

The amounts of starting nitrates and ammonium carbonate to be used in the above preparation of these catalysts, are shown in Table 1 below.

TABLE 1

| Catalyst | Starting nitrate Chemical formula | weight (g) | ammonium carbonate weight (g) |
|---|---|---|---|
| Catalyst 1 | $Y(NO_3)_3 \cdot 6H_2O$ | 101.8 | 60.6 |
| Catalyst 2 | $La(NO_3)_3 \cdot 6H_2O$ | 79.7 | 42.0 |
| Catalyst 3 | $Pr(NO_3)_3 \cdot 6H_2O$ | 79.1 | 41.5 |
| Catalyst 4 | $Nd(NO_3)_3 \cdot 6H_2O$ | 78.2 | 40.7 |
| Catalyst 5 | $Sm(NO_3)_3 \cdot 6H_2O$ | 76.5 | 39.3 |
| Catalyst 6 | $Y(NO_3)_3 \cdot 6H_2O$ | 33.9 | 40.4 |
|  | $Sm(NO_3)_3 \cdot 6H_2O$ | 39.3 |  |
| Catalyst 7 | $Y(NO_3)_3 \cdot 6H_2O$ | 41.4 | 49.3 |
|  | $Pr(NO_3)_3 \cdot 6H_2O$ | 47.0 |  |
| Catalyst 8 | $Y(NO_3)_3 \cdot 6H_2O$ | 58.3 | 52.1 |
|  | $Nd(NO_3)_3 \cdot 6H_2O$ | 33.4 |  |
| Catalyst 9 | $Y(NO_3)_3 \cdot 6H_2O$ | 79.0 | 56.5 |
|  | $La(NO_3)_3 \cdot 6H_2O$ | 17.9 |  |
| Catalyst 10 | $Y(NO_3)_3 \cdot 6H_2O$ | 31.3 | 46.3 |
|  | $Sm(NO_3)_3 \cdot 6H_2O$ | 36.1 |  |
|  | $Pr(NO_3)_3 \cdot 6H_2O$ | 17.7 |  |
| Catalyst 11 | $Sm(NO_3)_3 \cdot 6H_2O$ | 39.3 | 40.4 |
|  | $Pr(NO_3)_3 \cdot 6H_2O$ | 38.5 |  |
| Catalyst 12 | $Sm(NO_3)_3 \cdot 6H_2O$ | 64.1 | 39.5 |
|  | $Nd(NO_3)_3 \cdot 6H_2O$ | 12.6 |  |
| Comparative catalyst 1 | $Mg(NO_3)_3 \cdot 6H_2O$ | 190.8 | 169.8 |
| Comparative catalyst 2 | $Ce(NO_3)_3 \cdot 6H_2O$ | 79.4 | 41.7 |

In 100 ml of pure water, 25 g of magnesium hydroxide and 0.6 g of boron oxide were suspended, and heated at 90° C. while being stirred sufficiently, until achieving a clayey substance. The resultant was molded into tablets ($3\phi \times 5$ mm). After drying, the tablets were calcined at 600° C. for 2 hours, to give Comparative Catalyst 3 (Mg:B (atomic ratio)=100:4).

Synthesise of Unsaturated Alcohols

In a SUS reaction tube (inner diameter:16 mm) charged with 10 cc of the individual catalysts prepared in the above procedures, a mixture of acrolein and secondary butanol in a molar ratio of 1:5 was continuously supplied at 0.10 $hr^{-1}$ of L.H.S.V. (based on acrolein), followed by reacting at 300° C. for 10 hours at atmospheric pressure. The reaction products were analyzed using gas chromatography. The results are shown in Table 2 below.

TABLE 2

| Catalyst No. Component | Catalyst 1 $Y_2O_3$ | Catalyst 2 $La_2O_3$ | Catalyst 3 $Pr_2O_3$ | Catalyst 4 $Nd_2O_3$ | Catalyst 5 $Sm_2O_3$ | Compara. Catalyst 1 MgO | Compara. Catalyst 2 $Ce_2O_3$ | Compara. Catalyst 3 Mg—B—O |
|---|---|---|---|---|---|---|---|---|
| Acrolein conversion (%) | 26.5 | 24.6 | 27.8 | 24.7 | 28.1 | 23.9 | 19.1 | 23.8 |
| Selectivity (mol %) |  |  |  |  |  |  |  |  |
| allyl alcohol | 88.5 | 79.3 | 83.8 | 80.6 | 84.1 | 74.2 | 46.4 | 76.9 |
| propionic aldehyde | 7.3 | 11.8 | 11.0 | 11.0 | 8.4 | 11.3 | 32.2 | 9.7 |
| n-propanol | 0.4 | 0.1 | 0.6 | 0.1 | 0.4 | 1.1 | 0.1 | 0.7 |
| other by-products | 3.8 | 8.8 | 4.6 | 8.3 | 7.1 | 13.4 | 21.3 | 12.7 |

EXAMPLE 2

Catalysts 6 to 12 were prepared in the same manner as Example 1, except that mixed aqueous solution of nitrates of Y, La, Pr, Nd and Sm were used instead of $Y(NO_3)_3 \cdot 6H_2O$.

Using these catalysts, the same reaction as Example 1 was carried out. The compositions of the prepared catalysts and the analytical results of the reaction productions are shown in Table 3.

The amounts of starting nitrates and ammonium carbonate to be used in the preparation of Catalysts 6 to 12 are shown in Table 1 above.

TABLE 3

| Catalyst No. Component | Catalyst 6 $Y_2O_3$ $Sm_2O_3$ | Catalyst 7 $Y_2O_3$ $Pr_2O_3$ | Catalyst 8 $Y_2O_3$ $Nd_2O_3$ | Catalyst 9 $Y_2O_3$ $La_2O_3$ | Catalyst 10 $Y_2O_3$ $Sm_2O_3$ $Pr_2O_3$ | Catalyst 11 $Sm_2O_3$ $Pr_2O_3$ | Catalyst 12 $Sm_2O_3$ $Nd_2O_3$ |
|---|---|---|---|---|---|---|---|
| Composition (atomic ratio) | 1:1 | 1:1 | 1:0.5 | 1:0.2 | 1:1:0.5 | 1:1 | 1:0.2 |
| Acrolein conversion (%) | 28.5 | 27.7 | 25.5 | 26.3 | 30.3 | 28.3 | 28.3 |
| Selectivity (mol %) |  |  |  |  |  |  |  |
| allyl alcohol | 85.5 | 87.5 | 82.8 | 85.0 | 86.5 | 83.0 | 81.5 |
| propionic aldehyde | 8.0 | 8.7 | 10.1 | 9.8 | 7.7 | 9.2 | 10.2 |
| n-propanol | 0.3 | 0.6 | 0.2 | 0.5 | 0.3 | 0.4 | 0.2 |
| other by-products | 6.2 | 3.2 | 6.9 | 4.7 | 5.5 | 7.4 | 8.1 |

EXAMPLE 3

Using Catalyst 1 and Comparative Catalyst 1, long-duration continuous reactions were carried out in the same manner as Example 1, except that the reaction temperature were changed with the passage of reaction time. The results are shown in Table 4 below.

TABLE 4

| Reaction temp. (°C.) | Reaction time (hr) | Acrolein conversion (%) | Selectivity (mol. %) | | | |
|---|---|---|---|---|---|---|
| | | | allyl alcohol | propionic aldehyde | n-propanol | other by-products |
| Catalyst No. Catalyst 1 | | | | | | |
| Component $Y_2O_3$ | | | | | | |
| 300 | 4 | 39.0 | 86.3 | 7.8 | 0.6 | 5.3 |
| | 10 | 26.5 | 88.5 | 7.3 | 0.4 | 3.8 |
| 330 | 12 | 63.8 | 84.5 | 6.2 | 2.5 | 6.8 |
| | 50 | 50.2 | 85.8 | 7.4 | 1.7 | 5.1 |
| 340 | 54 | 67.9 | 85.1 | 6.5 | 3.3 | 5.1 |
| | 200 | — | — | — | — | — |
| | 1000 | 67.2 | 84.6 | 7.3 | 3.5 | 4.6 |
| Catalyst No. Comparative catalyst 1 | | | | | | |
| Component MgO | | | | | | |
| 300 | 4 | 48.0 | 73.5 | 10.7 | 2.1 | 13.7 |
| | 10 | 23.9 | 74.2 | 11.3 | 1.1 | 13.4 |
| 330 | 12 | 54.3 | 67.8 | 13.6 | 3.0 | 15.6 |
| | 50 | 34.0 | 68.5 | 14.5 | 2.2 | 14.8 |
| 340 | 54 | 52.6 | 61.6 | 17.4 | 5.5 | 15.5 |
| | 200 | 45.9 | 58.7 | 21.8 | 4.5 | 15.0 |
| | 1000 | — | — | — | — | — |

EXAMPLE 4

Catalysts 13–29, 33–49 and 53–56 were prepared in the same manner as Example 1, except that mixed aqueous solution of nitrates of Y, Sm, Mg, Ca, St, Cr, Mn, Fe, Co, Ni, Cu, Zn, Zr, Ag, Cd, Ba, Ce, Pb Bi and Sn were used instead of $Y(NO_3)_3.6H_2O$ as a starting material, with ammonium bicarbonate as a precipitant.

Using these catalysts, the same reaction as Example 1 was carried out. The compositions of the prepared catalysts and the analytical results of the reaction products are shown in Tables 5, 6 and 7.

EXAMPLE 5

An aqueous solution prepared by dissolving Y(-$NO_3)_3.6H_2O$ or $Sm(NO_3)_3.6H_2O$ in 250 ml of pure water at 40° C. was added to 500 ml of an aqueous solution containing ammonium bicarbonate, followed by reacting at 40° C. The resulting precipitate was filtered off, washed with pure water sufficiently, added to a solution prepared by dissolving or dispersing boron oxide, ammonium methavanadate or tin oxide while being stirred sufficiently, and then dried, followed by calcining at 600° C. for 2 hours.

Using the resulting calcined powder, Catalysts 30–32 and 50–52 were prepared in the same manner as Example 1.

Using these catalysts, the same reaction as Example 1 was carried out. The compositions of the prepared catalysts and the analytical results of the reaction products are shown in Tables 5 and 6.

TABLE 5

| Catalyst No. | Added element *1 | Acrolein conversion (%) | Selectivity (mol. %) | | | |
|---|---|---|---|---|---|---|
| | | | allyl alcohol | propionic aldehyde | n-propanol | other by-products |
| 13 | Mg | 24.0 | 87.9 | 8.8 | 0 | 3.3 |
| 14 | Ca | 25.1 | 86.2 | 10.3 | 0.3 | 3.2 |
| 15 | Sr | 23.8 | 86.8 | 9.3 | 0.3 | 3.6 |
| 16 | Cr | 20.3 | 87.9 | 8.8 | 0 | 3.3 |
| 17 | Mn | 31.1 | 90.6 | 6.6 | 0.3 | 2.5 |
| 18 | Fe | 22.1 | 85.9 | 11.0 | 0.7 | 2.4 |
| 19 | Co | 31.1 | 90.2 | 7.6 | 0.2 | 2.0 |
| 20 | Ni | 28.5 | 86.5 | 11.6 | 0.5 | 1.4 |
| 21 | Cu | 22.6 | 88.2 | 9.8 | 0 | 2.0 |
| 22 | Zn | 18.5 | 90.1 | 7.5 | 0.3 | 2.1 |
| 23 | Zr | 21.2 | 88.2 | 8.5 | 0 | 3.3 |
| 24 | Ag | 20.1 | 88.5 | 9.0 | 0.3 | 2.2 |
| 25 | Cd | 21.6 | 88.0 | 8.7 | 0 | 3.3 |
| 26 | Ba | 26.2 | 86.1 | 9.0 | 0.5 | 4.4 |
| 27 | Ce | 20.1 | 88.1 | 8.6 | 0 | 3.3 |
| 28 | Pb | 37.7 | 86.3 | 8.0 | 1.2 | 4.5 |
| 29 | Bi | 24.1 | 88.8 | 8.8 | 0 | 2.4 |
| 30 | B | 26.5 | 86.5 | 8.9 | 0.2 | 4.4 |
| 31 | V | 27.9 | 87.0 | 9.9 | 0.9 | 2.2 |
| 32 | Sn | 25.3 | 86.0 | 11.0 | 0.2 | 2.8 |

*1: Catalyst composition (atomic ratio) yttrium (Y):added element = 10:1

TABLE 6

| Catalyst No. | Added element *2 | Acrolein conversion (%) | Selectivity (mol. %) | | | |
|---|---|---|---|---|---|---|
| | | | allyl alcohol | propionic aldehyde | n-propanol | other by-products |
| 33 | Mg | 22.8 | 86.9 | 8.2 | 1.0 | 3.9 |
| 34 | Ca | 24.2 | 84.6 | 10.5 | 1.0 | 3.9 |
| 35 | Sr | 25.1 | 84.8 | 10.4 | 0.9 | 3.9 |
| 36 | Cr | 26.8 | 85.3 | 9.8 | 1.0 | 3.9 |
| 37 | Mn | 26.6 | 85.8 | 9.4 | 1.0 | 3.8 |
| 38 | Fe | 16.2 | 84.2 | 10.0 | 1.9 | 3.9 |
| 39 | Co | 30.6 | 84.6 | 10.3 | 1.3 | 3.8 |
| 40 | Ni | 27.7 | 85.6 | 9.4 | 1.1 | 3.9 |
| 41 | Cu | 29.0 | 85.1 | 10.0 | 1.1 | 3.8 |
| 42 | Zn | 28.2 | 85.4 | 9.8 | 1.0 | 3.8 |
| 43 | Zr | 23.3 | 85.2 | 10.1 | 0.9 | 3.8 |
| 44 | Ag | 25.2 | 85.8 | 9.6 | 0.7 | 3.9 |
| 45 | Cd | 20.7 | 84.5 | 10.0 | 1.6 | 3.9 |
| 46 | Ba | 24.7 | 85.0 | 9.7 | 1.4 | 3.9 |
| 47 | Ce | 21.8 | 85.6 | 9.6 | 1.0 | 3.8 |
| 48 | Pb | 40.0 | 84.5 | 8.6 | 2.1 | 4.8 |
| 49 | Bi | 26.0 | 85.1 | 9.8 | 1.3 | 3.8 |
| 50 | B | 27.6 | 85.6 | 9.9 | 0.9 | 3.6 |
| 51 | V | 26.9 | 85.7 | 9.3 | 1.3 | 3.7 |
| 52 | Sn | 23.2 | 84.4 | 10.1 | 1.6 | 3.9 |

*2: Catalyst composition (atomic ratio) samarium (Sm):added element = 10:1

TABLE 7

| Catalyst No. | Component composition | | | Acrolein conversion (%) | Selectivity (%) allyl alcohol |
|---|---|---|---|---|---|
| 53 | Y (10) | Ca (0.5) | Cu (0.5) | 27.5 | 87.1 |
| 54 | Sm (10) | Cd (0.2) | Mn (0.2) | 25.2 | 85.7 |
| 55 | Y (1) | Zn (1) | | 20.0 | 89.3 |
| 56 | Y (1) | Co (1) | | 35.3 | 89.5 |

The number in ( ) represents an atomic ratio of each element.

What is the claimed is:

1. A process for producing an unsaturated alcohol from an unsaturated aldehyde by a hydrogen transfer reaction with an alcohol, comprising the step of reacting an unsaturated aldehyde with a primary or secondary alcohol in the presence of a hydrogen transfer catalyst consisting of an oxide selected from the group consisting of oxides of Y, La, Pr, Nd, Sm and mixtures thereof.

2. The process of claim 1, wherein said catalyst is yttrium oxide.

3. The process of claim 1, wherein said catalyst is lanthanum oxide.

4. The process of claim 1, wherein said catalyst is praseodymium oxide.

5. The process of claim 1, wherein said catalyst is neodymium oxide.

6. The process of claim 1, wherein said catalyst is samarium oxide.

7. The process of claim 1, wherein said unsaturated aldehyde is an $\alpha,\beta$-unsaturated aldehyde.

8. The process of claim 7, wherein said aldehyde is selected from the group consisting of acrolein, methacrolein, crotonaldehyde, methyl vinyl ketone and cinnamaldehyde.

9. The process of claim 1, wherein said process is conducted at a temperature of 100°–500° C.

10. The process of claim 1, wherein the molar ratio of said alcohol to said aldehyde is 0.1–20.

11. The process of claim 1, wherein said process is a gas phase reaction and has a flow rate of 0.01–1 $hr^{-1}$.

12. A process for producing an unsaturated alcohol from an unsaturated aldehyde by a hydrogen transfer reaction with an alcohol, comprising the step of reacting an unsaturated aldehyde with a primary or secondary alcohol in the presence of a hydrogen transfer catalyst consisting of yttrium oxide, samarium oxide or mixtures thereof as the main active ingredient and a second oxide selected from the group consisting of oxides Ca, Sr, Ba, Mn, Cr, Fe, Co, Ni, Cu, Zn, Zr, Ag, Cd, Ce, Pb, Bi, B, V, Sn and mixtures thereof.

13. The process of claim 12, wherein said main ingredient is yttrium oxide.

14. The process of claim 12, wherein said main ingredient is samarium oxide.

15. The process of claim 12, wherein said main ingredient is a mixture of yttrium oxide and samarium oxide.

16. The process of claim 12, wherein said main ingredient is yttrium oxide and said second oxide is cobalt oxide, manganese oxide or a mixture thereof.

17. The process of claim 12, wherein said unsaturated aldehyde is an $\alpha,\beta$-unsaturated aldehyde.

18. The process of claim 12, wherein said aldehyde is selected from the group consisting of acrolein, methacrolein, crotonaldehyde, methyl vinyl ketone and cinnamaldehyde.

19. The process of claim 12, wherein said process is conducted at a temperature of 100°–500° C.

20. The process of claim 12, wherein the molar ratio of said alcohol to said aldehyde is 0.1–20.

21. The process of claim 12, wherein said process is a gas phase reaction and has a flow rate of 0.01–1 $hr^{-}$.

* * * * *